United States Patent [19]

Padula

[11] Patent Number: 5,620,862
[45] Date of Patent: Apr. 15, 1997

[54] METHODS FOR DIAGNOSING EARLY LYME DISEASE

[75] Inventor: Steven J. Padula, Simsbury, Conn.

[73] Assignee: University of Connecticut, Storrs, Conn.

[21] Appl. No.: 158,353

[22] Filed: Nov. 24, 1993

[51] Int. Cl.$^6$ .................................................. G01N 33/569
[52] U.S. Cl. ........................ 435/7.32; 435/7.92; 435/975; 436/513
[58] Field of Search .............................. 435/7.32, 7.92, 435/6, 975; 530/388.4, 389.5, 825; 436/513

[56] References Cited

U.S. PATENT DOCUMENTS

| | | | |
|---|---|---|---|
| 4,888,276 | 12/1989 | Shelburne | 435/7.32 |
| 5,187,065 | 2/1993 | Schutzer | 435/7.32 |
| 5,217,872 | 6/1993 | Dorward et al. | 435/7.32 |
| 5,246,844 | 9/1993 | Norris et al. | 435/172 |
| 5,308,753 | 5/1994 | Dorward et al. | 435/7.32 |

FOREIGN PATENT DOCUMENTS

| | | |
|---|---|---|
| 3942728 | 5/1991 | Germany . |
| WO91/09870 | 7/1991 | WIPO . |
| WO93/07897 | 4/1993 | WIPO . |

OTHER PUBLICATIONS

Marconi et al, "Identification of a Protein in several *Borrelia* species Which Is Related to Osp$^c$ of the Lyme Disease Spirochete", J. Clin. Microbiol., 31(10):2577–2583 (Oct. 1993).

Jauris–Heipke et al, "Genetic heterogenity of the genes coding for the outer surface protein C (OspC) and the flagellin of *Borrelia burgdorferi*", Med. Microbiol. Immunol., 182:37–50 (Mar. 1993).

Padula et al, "Use of Recombinant OspC from *Borrelia burgdorferi* for serodiagnosis of Early Lyme Disease", J. Clin. Microbiol., 32(7):1733–1738 (Jul. 1994).

Wilske et al, "Antigenic Variability of *Borrelia burgdorferi*", Ann. N.Y. Acad. Sci, 539:126–143 (1988).

Fikrig et al, "Elimination of *Borrelia burgdorferi* from vector ticks feeding on OspA–immunized mice", Proc. Natl. Acad. Sci. USA, 89(12):5418–5421 (Jun. 15, 1992).

Padula et al., "Molecular Characterization and Expression of p23 (OspC) from a North American Strain of *Borrelia burgdorferi*", Infection and Immunity 61(12):5097–5105 (Dec. 1993).

Fuchs et al., "Molecular Analysis and Expression of a *Borrelia burgdorferi* Gene Encoding a 22kDa Protein (pC) in *Escherichia coli*", Molecular Microbiology 6(4):503–509 (1992).

Sadziene et al., "The Cryptic ospC of *Borrelia burgdorferi* B31 is Located on a Circular Plasmid", Infect. Immun. 61(5):2192–2195 (1993).

Marconi et al., "Transcriptional Analyses and Mapping of the ospC Gene in Lyme Disease Spirochetes", Journal of Bacteriology 175(4):926–932 (Feb. 1993).

Dressler et al., "Western Blotting in the Serodiagnosis of Lyme Disease", The Journal of Infectious Diseases 167:392–400 (1993).

Wilske et al., "An OspA Serotyping System for *Borrelia burgdorferi* Based on Reactivity with Monoclonal Antibodies and OspA Sequence Analysis", Journal of Clinical Microbiology 31(2):340–350 (Feb. 1993).

Wilske et al., "Immunological and Molecular Polymorphisms of OspC, an Imunodominant Major Outer Surface Protein of *Borrelia burgdorferi*" Infect. Immun. 61:2182–2191 (1993).

Padula et al., "Cloning and Expression of p25 from *Borrelia Burgdorferi* (8B)—A Potential New Target . . . ", Arthritis & Rheumatism 34:S184 Abstract (Sep. 1992).

Preac–Mursic et al., "Active Immunization with pC Protein of *Borrelia burgdorferi* Protects Gerbils against *B. burgdorferi* Infection", Infection 20:342–348 (1992).

Aguero–Rosenfeld et al., "Serodiagnosis in Early Lyme Disease", J. Clin. Micro. 31:3090–3095 (Dec. 1993).

Dias et al., "Interpretation of IGM Western Immunoblot Banding Patterns in Patients Suspected of Having Early Lyme Disease", V. International Conference on Lyme Borreliosis, May 30–Jun. 2, 1992, Abstract.

Livey et al., "Identification and Characterization of a Protective Antigen from *B. burgdorferi*", V International Conference on Lyme Borreliosis Program and Abstract, p. A63, Abs. #370, 1992.

*Primary Examiner*—Marian C. Knode
*Assistant Examiner*—Donna C. Wortman
*Attorney, Agent, or Firm*—Hamilton, Brook, Smith & Reynolds, P.C.

[57] ABSTRACT

The invention relates to DNA encoding *Borrelia burgdorferi* sensu stricto outer surface protein C. Purified and recombinant forms of a 23 kDa protein from a Connecticut isolate of *B. burgdorferi* are described. The 23 kDa protein, referred to as p23 or OspC, can be used for immunodiagnostic assays for detection of early Lyme disease. The protein, amino acid coding for the protein and DNA sequences can be used to prevent Lyme disease, to diagnose/detect *B. burgdorferi* in human or animal tissues or body fluids. Antibodies specific for the protein can also be generated.

4 Claims, 2 Drawing Sheets

```
AGGGAATTTAGCATATATTTGGCTTTGCTTATGTCGATTTTAAAATCAAATTAAGTCAATATTTTTCAAATTCTTCAATATT     80
                                        ▲
                                                                    -10
TATTCAATATATTGAATAAATTGAAAAAATTATTTTTCAAATAAAAAATTGAAAACAAAATTGTTGACTAATAATTC          160
       ▼                     -35
                                       M  K  K  N  T  L  S  A  I  L  M  T  L  F  L  F  I  S  C
ATAAATAAAAAGGAGGCACAAATTAATGAAAAAGAATACATTAAGTGCAATATTAATGACTTTATTTTTATTTATATCTT      240

N  N  S  G  K  D  G  N  T  S  A  N  S  A  D  E  S  V  K  G  P  N  L  T  E  I
GTAATAATTCAGGGAAAGATGGGAATACATCTGCAAATTCTGCTGATGAGTCTGTTAAAGGGCCTAATCTTACAGAAATA      320
                                                                              ▲
 S  K  K  I  T  E  S  N  A  V  V  L  A  V  K  E  V  E  T  L  L  A  S  I  D  E  V
AGTAAAAAAATTACAGAATCTAACGCAGTTGTTCTCGCCGTGAAAGAAGTTGAAACTCTGCTTGCATCTATAGATGAAGT      400
                                              p1                                    ▲
 A  K  K  A  I  G  N  L  I  A  Q  N  G  L  N  A  G  A  N  Q  N  G  S  L  L  A  G
TGCTAAGAAAGCTATTGGGAATTTGATAGCCCAAAATGGTTTAAATGCCGGTGCTAATCAAACGGATCATTGTTAGCGG     480
                               p2
 A  Y  V  I  S  T  L  I  A  E  K  L  D  G  L  K  N  S  E  E  L  K  E  K  I  E
GAGCCTACGTAATATCAACCCTAATAGCAGAGAAATTAGATGGATTGAAAAATTCAGAAGAATTAAAGGAAAAAATTGAA     560

D  A  K  C  N  K  A  F  T  D  K  L  K  S  H  A  E  L  G  I  A  N  G  A  A
GATGCTAAAAAATGTAACAAAGCATTTACTGATAAACTAAAAAGTAGTCATGCGGAACTCGGTATAGCGAATGGAGCTGC     640

T  D  A  N  A  K  A  A  I  L  K  T  N  G  T  K  D  K  G  A  Q  E  L  E  K  L  F
TAGTGATGCTAATGCAAAAGCGGCTATTTTAAAAACAAATGGTACTAAAGATAAAGGGTGCTCAAGAGCTTGAAAAGTTAT     720

E  S  V  K  N  L  S  K  A  A  Q  E  T  L  N  N  S  V  K  E  L  T  S  P  V  V
TTGAATCAGTAAAAAACTTGTCAAAAGCAGCTCAAGAAACACTAAATAATTCAGTTAAAGAACTTACAAGTCCTGTTGTG     800

A  E  N  P  K  K  P  *
GCAGAGAAATCCAAAAAAAACCTTAA                                                           824
```

Figure 1

```
                           71                              141                            212
2591:  MKKNTLSAILMTLFLFISCNNSGKDG-NTSANSADESVKGPNLTEISKKITESNAVVLAVKEVETLLASIDE
B31:   ****************************--*****-****************D****L***A***S****
PKo:   *****************************G*DSA*T*P****A***************D*F*****VL****

2591:  VAKKAIGNL-IAQN-GLNAGANQNGSLLAGAYVISTLIAEKLDGLNSEELKEKIEDAKKCNKAFTDKLKSS
B31:   I*A****KK-*H*NDTEN*H************A****-*G*****-*DA**SETN***EK
PKo:   L*****QKIDNN--A*LN***A***T*SKL***TE*AK**SEEN*****G

2591:  HAELGIANGAATDANAKAAILKTNGTKDKGAQELEKLFESVRNLSKAAQETLNNSVKELTSPVVAENPKKP
B31:   *TD--XEGVDE********TE*G****EV*****K*M*A********S**
PKo:   D-KQD*--DH*****HA*T****K*FKD*****EG*L*****VA*T************S**

Figure 2
```

METHODS FOR DIAGNOSING EARLY LYME DISEASE

GOVERNMENT SUPPORT

Work described herein was supported in whole or in part by a grant from Public Health Service (Grant No. #5R29-AR39361). The Government has certain rights in this invention.

BACKGROUND

Lyme disease is a multisystem infection caused by the tick-borne spirochete, *B. burgdorferi* (Steere, 1989). Because of the low yield of both culture and direct visualization techniques for identification of this organism, the diagnosis of Lyme disease has relied on serologic confirmation in patients with characteristic clinical findings.

Recognizing Lyme disease in the early stages can be difficult, however, because patients may not manifest the characteristic rash or may have only non-specific flu-like symptoms. This difficulty of diagnosis is compounded by the delayed emergence of a humoral response to the spirochete as detected by available serologic tests (Steere, 1989). These tests, which currently lack standardization, also do not readily distinguish between reactivity to *B. burgdorferi* proteins and cross-reactive proteins from commensual or other pathogenic organisms (Hansen et al., 1988; Magnarelli et al., 1987). Delay in establishing the diagnosis of Lyme disease in its early stages is clinically important because timely institution of appropriate antibiotic treatment can prevent the serious sequelae from this potentially chronic infection (Dattwyler et al., 1990; Steere et al., 1983).

Initial studies with immunoblot analysis of patients from North America with the early manifestations of Lyme disease found IgM reactivity predominantly against the 41 kDa flagellar protein of *B. burgdorferi* (Barbour et al., 1986; Craft et al., 1986). In hope of improving the level of detection of the antibody response in early Lyme disease, studies have utilized enriched preparations and recombinant forms of the 41 kDa flagellar protein as target antigen for serologic testing (Magnarelli et al., 1992; Coleman et al., 1987). This approach was prompted by the initial immunoblot studies with *B. burgdorferi* lysates in which an early and predominant IgM antibody response to the flagellar protein was demonstrated by Craft et al., 1986. Use of the flagellar protein-based serologic tests may be problematic because of the relatively frequent finding of cross-reactive antibodies to conserved flagellar epitopes from commonly occurring commensual and pathogenic spirochetes, such as those found in the mouth (Magnarelli et al., 1990; Russell et al., 1984).

Dressler et al. reported the most prominent IgM response in American patients with early disease was to a 21 kDa protein. This protein was reported to be reactive with a monoclonal antibody specific for pC. This finding contrasts with this same group's previous finding of a predominant early response to the 41 kDa flagellar antigen (Craft et al., 1986). The discrepency between these two findings was attributed to different antigen preparations despite the use of the same isolate, highlighting the potential confusion introduced by the current lack of test standardization.

Recently, Marconi et al. and Sadziene et al. localized the OspC gene to a 26–27 kDa circular plasmid, the first gene mapped to a circular plasmid in *B. burgdorferi*. Marconi et al. mapped the gene by using a variety of electrophoretic separation techniques and Southern blotting. Sadziene et al. used a group of B31-derived isolates which contained their linear chromosome and circular plasmids, but had been antibody-selected for the loss of a variable number of their linear plasmids. Sadziene et al. also found a correlation of an isolate's ability to express OspC and the loss of a linear plasmid of 16 kb (lp16). They hypothesized that a protein or RNA encoded by lp16 may function as a repressor of OspC expression. Loss of this plasmid could thereby lead to the loss of repression and new expression of the protein. In addition, these workers noted that the loss of lp16 also led to a failure of the mutant to grow on solid medium.

SUMMARY OF THE INVENTION

This invention is based upon the discovery that sera from patients with early Lyme disease contain predominant IgM reactivity to a major 23 kDa protein (p23; also referred to herein as OspC) from *Borrelia burgdorferi* strain 2591, an isolate found in Connecticut. This strain was found to abundantly produce OspC. The p23 gene from strain 2591 was cloned and sequenced. The protein deduced therefrom contained 212 amino acids and had a molecular weight of 22,250 kDa. Purified and recombinant forms of OspC protein were produced as a target antigen and tested in Enzyme Linked Immunosorbant Assay (ELISA) and Western Blot assays.

Detection of *B. burgdorferi*-specific IgM antibodies in 74 individuals with culture positive erythema migrans and 76 controls without Lyme disease were determined using a whole cell (WC) ELISA, immunoblot and recombinant OspC (rOspC) ELISA. With all test results there was a statistically significant association between the duration of disease and the frequency of a positive result. The rOspC ELISA had a positive predictive value of 100% and a negative predictive value of 74%. Simlar results were obtained with the whole cell ELISA and immunoblot.

Based upon these results, recombinant p23 can be used in diagnostic assays (serological and cellular) to detect early stages of Lyme disease. Methods for detecting early Lyme disease, diagnostic reagents therefor, kits containing the reagents, and method for preventing Lyme borreliosis are described. The invention provides the advantages of immunoassay standardization due to use of recombinant forms of OspC; early detection of the humoral response in infected individuals; and antigen uniformity due to phenotype stability of strain 2591. The rOspC ELISA is equally or more sensitive and specific than currently used diagnostic tests for early Lyme disease.

BRIEF DESCRIPTION OF THE DRAWINGS

FIG. 1. Nucleotide sequence of the p23 gene from strain 2591 and the deduced amino acid sequence in single letter designation are shown. The sequences of the 2 tryptic peptide fragments obtained from 2591 (p1 and p2) are overlined. Consensus -10 and -35 promoter hexamers from *E. coli* and the consensus ribosomal binding site (heavy underline) are shown. The downward pointing arrow designates the transcriptional start site as determined by primer extension analysis. The sequence between the horizontal arrows (nucleotide position 60 to 113) designates the deletion in strain B31. The sequence complementary to the 17-mer oligonucleotide used for primer extension and Northern blot analysis is shown in bold-faced print (nucleotide position 242 to 258). The stop codon (TAA) is marked by an asterisk. (SEQ ID NO:1) (GenBank Accession Number U01892).

FIG. 2. Comparison of the amino acid sequences of OspC (p23 and pC) from 3 different *B. burgdorferi* isolates is shown. The upper sequence corresponds to strain 2591 (SEQ ID NO:2); the middle sequence corresponds to strain B31 (SEQ ID NO:3); and the bottom sequence corresponds to strain PKo (SEQ ID NO:4; Dressler et al., 1993). Identity of the amino acid sequence in B31 and PKo with 2591 is indicated by an asterisk below the designated position. Amino acid subsitutions are represented by the placement of an appropriate letter below the position. Spaces (-) have been included to optimize the match among the proteins.

DETAILED DESCRIPTION OF THE INVENTION

The invention pertains to DNA encoding outer surface protein C (OspC) of *Borrelia burgdorferi* sensu stricto and North American strains of *B. burgdorferi,* to substantially purified and recombinant forms of OspC, to compositions containing OspC, to methods for making the protein, to methods for diagnosing/detecting *B. burgdorferi* in human or animal biological fluids and to reagents and test kits therefor. Antibodies raised against the OspC protein are described as well as use of the antibodies for detecting/screening the presence of *B. burgdorferi* in ticks, for example.

The invention is based upon the discovery that *Borrelia burgdorferi* strain 2591, a Connecticut isolate, abundantly expresses OspC. This is unique in contrast to most North American strains of *B. burgdorferi* which do not express the OspC protein. For example, strain B31 is commonly used as a serologic assays for Lyme disease. OspC is an immunodominant antigen as it elicits a humoral antibody response in mammals with early Lyme disease. Thus, purified and recombinant forms of the OspC protein can be used as a diagnostic tool for screening/detecting early Lyme disease.

Based upon this discovery, the gene encoding p23 was cloned as a fusion protein, sequenced and found to be 83% identical by nucleotide sequence and 75% identical by amino acid sequence to pC (recently renamed OspC), an abundantly expressed protein on the outer surface of PKo, a European strain of *B. burgdorferi* (Wilske et al., 1993). The protein was predicted to contain 212 amino acids with a molecular weight of 22,250 kDa. The nucleotide sequence and its predicted amino acid sequence are shown in FIG. 1 (SEQ ID NO:1). In addition, immunoelectron microscopy localized p23 to the outer membrane, confirming that p23 is the strain 2591 homolog of OspC.

In another aspect of the invention, Northern blot analysis was used to detect low levels of OspC mRNA in the North American strain B31. DNA sequencing of the OspC gene from B31 revealed a 54 bp deletion in the upstream regulatory region, possibly accounting for the low transcriptional activity of OspC. The OspC coding region from B31 was cloned and antibody reactive OspC was expressed in *Escherichia coli.* The amino acid sequence for strain B31 is shown in FIG. 2 (SEQ ID NO:2). To determine whether the coding region of OspC from B31 is capable of encoding an immunologically detectable protein, recombinant OspC from B31 in *E. coli* was expressed. Patient sera and MAbs reactive with p23 (OspC) from strain 2591 were found to be strongly reactive with recombinant OspC from strain B31.

Because of the observation that p23 from strain 2591 is an early immunodominant target of the humoral response in Lyme disease, a recombinant form of the protein was produced for testing in diagnostic assays. Preliminary studies with recombinant p23 indicate that it can be used as a sensitive and specific antigen for serologic detection early in disease.

The results from this preliminary study showed that 15 out of 15 sera from patients with clinically suspected Lyme disease and positive immunoblots were strongly reactive with rOspC. Five sera from patients with syphilis, 10 sera containing high-titered rheumatoid factor, 5 sera from patients with Epstein-Barr virus infection, and 10 sera from systemic lupus erythematosus patients with high-titered antinuclear antibodies were all negative for anti-rOspC. These results clearly shown that rOspC is specific for antibody to *B. burgdorferi* and is not cross-reactive to commensual or other pathogenic organisms.

A more extensive clinical study was also carried out on a large panel of sera obtained from patients with culture-positive erythema migrans (EM) as well as a control group including patients from a non-endemic area for Lyme disease and patients with severe perodontitis. As shown in Table 5 in the Example Section, there was a positive correlation between duration after EM onset and the frequency of positive results, regardless of the assay used. For the entire group of Lyme disease sera, the sensitivities of the immunoblot, regardless of the criteria used for a positive result, and the rOspC ELISA were equivalent (approximately 65%) and slightly better than the WC ELISA (58%) (Table 6). The specificities of all three tests including the immunoblot, using criteria of ≧3 bands with or without the 23 kDa band, were 100% or nearly so (Table 6).

It is important to recognize that the source of antigen for the immunoblot and WC ELISA was strain 2591, a producer of abundant levels of OspC. Use of this strain may therefore have led to increased sensitivities with these assays compared to the use of a non-expressing strain. Poorer test performance was observed when directly comparing B31 (OspC-negative)- and 2591-based assays.

There were a number of sera in which there was a discrepancy between the observed reactivity to the 23 kDa protein by blot and the rOspC by ELISA. In most of these cases there was very faint reactivity found on blot and negative reactivity with rOspC by ELISA. This highlights the difficulties introduced when evaluation of band reactivity and interpretation of a positive blot is performed subjectively. This finding was most frequent among the negative controls and might be an important source of false positive results using immunoblots. Explanation of the rarer situation of reactivity to rOspC and no band seen on blot (e.g., patient #6) is more difficult. Although strain 2591 served as both the source of the antigen used for the blots and the source of the gene used for expression of rOspC, there may be some differences in the expressed epitopes. The rOspC is expressed as a fusion protein and coexpression of the carrier protein may influence the availability of immuno-reactive sites.

Based upon these findings, rOspC can be used as a diagnostic tool for determining the presence of *B. burgdorferi* specific antibodies in mammals, preferably humans. A diagnostic method will include: a) contacting a biological sample (e.g., blood, urine, tissue, cerebrospinal fluid, serum, pericardial fluid or synovial fluid) from a mammal suspected of having Lyme disease with a recombinant purified form of OspC from *B. burgdorferi;* and b) detecting the presence or absence of a complex formed between the protein and antibody specific therefor. The presence of antibody-antigen complex is indicative of infection by the spirochete (current infection or past infections) in the mammal. This method allows for early detection of Lyme borreliosis because the early stages of infection result in the production of IgM antibodies to the spirochete. These antibodies are reactive to the purified and recombinant proteins described herein.

Suitable serologic assays that can be used to diagnose early Lyme disease include, but are not limited to, ELISA, Western Blot, amplified ELISA and capture ELISA. Methods for performing these assays are well known in the art. Diagnostic kits are also contemplated and comprise recombinant or substantially pure forms of OspC, optionally in conjunction with other *B. burgdorferi* outer surface proteins (OspA, OspB and p41), and ancillary reagents suitable for use in detecting the presence of antibodies to the protein in a biological sample. Ancillary reagents will be readily apparent to the skilled artisan based upon the type of immunoassay to be performed.

Alternative to serologic diagnostic methods, cellular based assays can be used to detect reactivity to OspC for determining infection. An example of a cellular assay is a mononuclear proliferation assay which can be performed using known techniques and in which the antigen is OspC.

Biological tools, such as DNA encoding OspC, vectors containing the DNA, host cells stably transformed by the vector, peptides and proteins, can be made according to standard techniques. For example, the DNA can be cloned or chemically synthesized. The OspC protein or peptides thereof can be obtained in quantities suitable for diagnostic assays by purification techniques or recombinantly by a) culturing host cells that express OspC under conditions suitable for expression; and b) isolating the expressed protein from the host cells. An example of a suitable host cell is *Escherichia coli.*

Antibodies (polyclonal or monoclonal) can be raised against OspC and used as a tool for screening the presence or absence of spirochetes in biological samples or whether a tick is infected with *B. burgdorferi.* In the case of ticks, the tick could be crushed to release the spirochetes which in turn would complex with the antibody. Presence of antigen-antibody complex is indicative of infection. Known techniques can be used to perform this screening method, such as using an immunofluorescent labeling and detecting fluorescence.

The present invention also relates to compositions for use in vaccine preparations. General concepts related to methods of preparation and use are discussed as applicable to preparations and formulations with the disclosed 23 kDa antigen, its epitopes and subfragments thereof. In one embodiment, the composition will comprise OspC (pure or recombinant forms) in a physiologically acceptable vehicle(s). The composition can optionally contain other outer surface proteins from *Borrelia burgdorferi,* such as OspA, OspB and p41.

Preparation of vaccines which contain peptide sequences as active ingredients is generally well understood in the art. Typically such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredients, preferably 25–70%.

The proteins may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amounts as will be therapeutically effective and immunogenic. The quantity to be administered depends on the subject to be treated, including, e.g., the capacity of the individual's immune system to synthesize antibodies, and the degree of protein desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable but are typified by an intial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine include use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperature ranging between 70° C. to 101° C. for 30 seconds to 2 minute periods respectively. Aggregation by reactivating with pepsin treated (Fab) antibodies to albumin, mixture with bacterial cells such as *C. parvum* or endotoxins or lipopolysaccharide components of gram negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932, 4,174,384 and 3,949,064, as illustrative of these types of assays.

The invention provides many advantages over immunological assays currently available for detection of Lyme disease. Use of rOspC in an ELISA is a convenient, readily automated and easily standardized test for serodiagnosis of early Lyme disease. The diagnostic reagents described herein can be reliably used to detect humoral response in the early stages of infection. Such early detection will afford early antibiotic intervention and will reduce further complications of the disease. The antigens have been shown to be specific for antibodies raised to OspC of *B. burgdorferi* but yet are not crossreactive to proteins from commensual or other pathogenic organisms. Clinical studies strongly affirm this observation. This distinction is necessary for timely and accurate diagnosis of Lyme disease.

The invention will be further illustrated by the following nonlimiting examples.

EXAMPLES

I. Moleculer Characterization and Expression of p23 (OspC)

*B. burgdorferi* strains and antigen preparation.

*B. burgdorferi* strain 2591 was obtained from L. Magnarelli, Department of Entomology, The Connecticut Agricultural Experiment Station, New Haven, Conn. It was initially isolated from a white-footed mouse caught in East Haddam, Conn.; *B. burgdorferi* type strain B31 was obtained from American Type Culture Collection (Rockville, Md.) (ATCC 35210). The spirochetes were grown in BSK II medium in a closed flask at 33° C. as previously described (Barbour et al., 1984). After 10–14 days of growth, the organisms were washed 3 times in Dulbecco's phosphate buffered saline (DPBS) (Gibco, Grand Island, N.Y.) and sonicated on ice by a cell disruptor (Branson Model 185, Danbury, Conn.) using ten 15-sec blasts at 60% of maximum power. The sonicate was cleared by centrifugation at 10,000×g and 4° C. for 20 min. The protein concentration in the supernatant was determined by the Bradford method (Bradford 1976).

Genomic DNA Isolation.

Washed spirochetes were suspended in buffer (25% sucrose, 50 mM Tris-HCl pH 7.5, 5 mM $Na_2EDTA$) and lysed by adding sodium dodecyl sulfate (SDS) (final concentration of 0.5%), RNAase A (0.1 mg/ml), and Proteinase K (0.1 mg/ml) for 45 min at 37° C. with gentle agitation. The DNA was extracted 2 times with buffered phenol and 1 time with phenol and chloroform/isoamyl alcohol (24:1) and ethanol precipitated.

Polyacrylamide electrophoresis and electroelution.

*B. burgdorferi* sonicate (40–80 µg/lane, 0.8 mm thickness and 80 mm width) was mixed with an equal volume of sample buffer (0.125M Tris-HCl pH 6.8, 4% SDS, 20% glycerol, 2% 2-mercaptoethanol, 0.001% bromophenol blue), boiled for 5 minutes, and subjected to electrophoresis in a discontinuous 0.1% SDS—12% polyacrylamide slab gel (PAGE) with buffers described by Laemmli, 1970. Molecular mass standards included myosin (200,000 kDa), *E. coli* β-galactosidase (116,250 kDa), rabbit muscle phosphorylase b (97,400 kDa), bovine serum albumin (66,200 kDa), hen egg white ovalbumin (45,000 kDa), bovine carbonic anhydrase (29,000 kDa), soybean trypsin inhibitor (21,500 kDa), and hen egg white lysozyme (14,400 kDa). Gels were stained and fixed with 0.25% Coomassie Brilliant Blue R in 50% methanol and 10% acetic acid and destained with 40% methanol and 10% acetic acid. For the preparative gel, 50/µg–825/4 g of protein was added to a 1.5 mm×140 mm well. The band corresponding to p23 was visualized by precipitation with cold 0.1M KCl and was cut from the remainder of the gel. The protein was isolated by electroelution and dialyzed successively against 0.02M ammonium bicarbonate/0.1% SDS for 12 hours and 0.1M ammonium bicarbonate/0.02% SDS for 12 hours. The protein concentration was determined by the BCA protein assay (Pierce Chemical Co., Rockford, Ill.).

Immunoblot analysis.

Proteins separated by SDS-PAGE were transferred to nitrocellulose and incubated with sera or supernatants containing monoclonal antibody by a modification of the method described by Towbin et al., 1979. Transfer of the proteins to nitrocellulose (Bio-Rad Laboratories, Hercules, Calif.) was performed in a Trans-Blot cell (Bio-Rad Laboratories) containing 192 mM glycine, 25 mM Tris base, and 20% methanol at 0.5 amps for 1 hour with cooling. The transferred proteins were visualized by staining the nitrocellulose membrane with 0.5% Ponceau S in 1% glacial acetic acid. Nonspecific binding to the blots was blocked by incubating for 1 hour at 20° C. in tris buffered saline (TBS) (20 mM 5 Tris-HCl pH 7.5, 150 mM NaCl) with 1% bovine serum albumin (BSA). The blots were washed 3 times with TBST (TBS with 0.05% Tween-20) and then incubated with patient sera (1:100 in TBS/1% BSA) or hybridoma supernatant (1:5 in TBS/1% BSA) for 1 hour at 20° C. After the blots were washed 4 times with TBST, they were incubated with goat anti-mouse IgM and IgG (heavy and light chain) conjugated to alkaline phosphatase (Kirkegaard and Perry Laboratories, Gaithersburg, Md.) or goat anti-human γ-chain and anti-human µ-chain conjugated to peroxidase (Sigma, St. Louis, Mo.). The blots were then washed 4 times with TBST, and substrate (NBT/BCIP for alkaline phosphatase conjugate or 3,3'diaminobenzidine/hydrogen peroxide for peroxidase conjugate) was added.

Partial amino acid sequence determination of p23.

Trypsin digestion was performed as previously described by Ozols 1990. Briefly, the electroeluted protein was lyophilized, resuspended in 20% trichloroacetic acid and precipitated at 4° C. for 12 hours. After centrifugation, the pellet was resuspended in cold 0.5 ml of 0.2% HCl in acetone, and incubated at −20° C. for several days. After two washes with cold acetone the protein (approx. 25 µg) was dried at 20° C. and digested with 0.25 nmole of trypsin (Worthington, Freehold, N.J.) in 2.3M urea, 0.1M Tris-HCl pH 8.06, 0.2M ammonium bicarbonate for a maximum of 24 hours at 20° C. The peptide mixture was resolved by reverse phase HPLC (Ozols et al. 1980). The sequence analysis of the peptides was carried out on an Applied Biosystems Model 470A gas-phase sequencer equipped with Model 120A PTH analyzer according to instructions from the manufacturer.

Isolation of the gene encoding p23.

Degenerate oligonucleotide primers were synthesized based on the amino acid sequence of 2 trypsin-digested peptide fragments. The polymerase chain reaction (PCR) was used to amplify the intervening segment of DNA between the two primers—upstream primer 5'-GTATAAG-GAGGTATGAAGAC-3' (SEQ ID NO:5) and downstream primer 5'-CCGTTTCTGAGTTGATCGCGATCCC-3' (SEQ ID NO:6). Amplification was performed in a volume of 100 μl in a thermal controller (MJ Research, Watertown, Mass.) at the following conditions: 94° C.×5 minutes, 40° C.×1 minute, 72° C.×1 minute, 94° C.×1 minute, 39° C.×1 minute, 72° C.×1 minute, (94° C.×1 minute, 38° C.×1 minute, 72° C.×1 minute for 30 cycles) and 72° C.×5 minutes for extension. Each primer was used at a final concentration of 0.5 μM and 50 ng of genomic DNA was used as template. The amplification buffer included 50mM KCl, 20mM Tris-HCl pH 8.4 (at 25° C.) 2 mM $Mg_2Cl$, 0.1 mg/ml BSA 0.125 nM of each dNTP, and 2.5 U of Taq DNA polymerase. The amplified DNA was radiolabeled by the random primer technique and used to probe a Southern blot of genomic *B. burgdorferi* DNA separately restricted with 8 different restriction enzymes. Genomic DNA was cut with the appropriate restriction enzyme and the corresponding sized fragments were isolated from low melt agarose and cloned into pBS (Stratagene, La Jolla, Calif.) and transformed into DH5α (BRL, Gaithersburg, Md.). The radiolabeled PCR amplified fragment was used to probe the selected library by colony hybridization and positive colonies were grown, and the cloned insert was sequenced in both orientations by dideoxy chain termination with Sequenase v.2.0 (US Biochemical, Cleveland, Ohio).

Northern blot analysis and transcriptional start site.

Total cellular RNA was obtained from the spirochetes in the presence of diethylpyrocarbonate as previously described in Summers, 1970. RNA (15 μg/lane) was electrophoresed in a 0.66M formaldehyde/MOPS 1% agarose denaturing gel, transferred to a nylon membrane (NYT-RAN™, Schleicher and Schuell, Keene, N.H.) and hybridized to a synthetic 17-mer oligonucleotide (5'-CTTTCCCT-GAATTATTA-3')(SEQ ID NO:7), complementary to a sequence which is identical in strains 2591 and B31. The oligonucleotide was 3'-labeled with digoxigenin and prehybridization and hybridization was performed at 42° C. as recommended by the manufacturer (The Genius System, Boehringer Mannheim Corp. Indianapolis, Ind.). The membrane was washed twice in 6×SSC (1×SSC=0.15M NaCl and 0.015M sodium citrate), 0.05% PPi at 20° C. for 5 minutes and twice in 6×SSC, 0.0.5% PPi at 42° C. for 15 minutes. Immunodetection of the oligonucleotide with an alkaline phosphatase-conjugated anti-digoxigenin antibody and visualization by chemiluminescense was performed as per the manufacturer's recommendations.

The transcriptional start site for the p23 gene was determined by primer extension analysis (Jones et al., 1985; McKnight et al., 1982). The 17-mer primer used in the Northern blot analysis was 5'-labeled with [γ-$^{32}$]ATP (Amersham, Arlington Heights, Ill.) and T4 polynucleotide kinase (BRL) and separated from unincorporated label with a G25 spin column (Select-D, 5Prime→3Prime, Boulder, Colo.). Three pmoles of the labeled primer was mixed with 15 μg of RNA in 3 μl of hybridization buffer (100 mM KCl, 50 mM Tris-HCl pH 8.3), heated to 90° C. for 5 minutes, annealed at 42° C. for 10 minutes, and placed on ice for 15 minutes. One μl of 5×reverse transcriptase buffer (250 mM Tris-HCl pH 8.3, 200 mM KCl, 15 mM $MgCl_2$, 10 mM DTT and 1 mM each dNTP) and 1 μl of RNaseH reverse transcriptase (Superscript, BRL) were added to the annealed reaction and incubated at 42° C. for 1 hour. Five μl of stop solution (95% formamide, 20 mM EDTA, 0.05% bromophenol blue, 0.05% xylene cyanol FF) was added and half of the volume was loaded onto a 6% polyacrylamide sequencing gel. The sizes of the extended products were determined by comparison with a DNA sequencing ladder obtained with the 17-mer oligonucleotide primer and a plasmid containing the p23 gene.

Expression of p23 as a fusion protein.

Genomic DNA was used as template for PCR amplification of p23 with primers based on the sequenced DNA. The product was cloned into the SmaI site of the expression vector pGEX-2T (Pharmacia—LKB, Piscataway, N.J.) for expression as a fusion protein with glutathione S-transferase at the amino-terminus to faciltate affinity purification. The cloned gene was sequenced to confirm that it had been inserted in the appropriate reading frame. Colonies were grown overnight in 2 ml of super-broth (32 g tryptone, 20 g yeast extract, 5 g NaCl, 5 ml NaOH per liter) and the next day isopropyl β-D-thiogalactoside (IPTG) (Sigma) was added to 0.1 mM and the culture was grown for an additional 2 hours. The cells were pelleted, resuspended in cold DPBS, and sonicated. The supernatant was cleared by centrifugation and 50 μl of 50% (w/v) of glutathione-agarose beads (Sigma) was added to the supernatant and mixed gently at 20° C. for 10 minutes. The beads were washed 3 times with DPBS, resuspended in SDS-PAGE sample loading buffer and run in a 12% SDS-PAGE.

Use of recombinant p23 in an ELISA.

Large scale preparation of the p23 fusion protein was performed as above with the additional step of elution of the protein from the beads with 5 mM reduced glutathione (Sigma) in 50 mM Tris-HCl (pH8.0). Sixty μl of the fusion protein (5 μg/ml) in DPBS was added to alternate wells of a flat-bottom microdilution plate (Nunc-Immunoplate; Marsh Biomedical Products, Rochester, N.Y.) for 12 hours at 4° C. An equimolar amount of the carrier protein in DPBS was added as a control antigen to the remaining wells. The plates were blocked for 1 hour at 37° C. with 200 μl of DPBS containing 0.05% horse serum and 0.01% dextran sulfate. The plates were washed 6 times with DPBS with 0.05% Tween-20 (DPBST). Patient sera were serially diluted twofold from 1:20 to 1:1280 in DPBST. Positive and negative control sera were included on each plate. After addition of sera, the plates were incubated for 1 hour at 37° C. and then washed 6 times in DPBST. The secondary antibody used was goat anti-human IgM (μ chain specific) conjugated to peroxidase (Sigma) diluted in DPBST. For screening the hybridoma supernatants for monoclonal antibodies the secondary antibody used was goat F(ab')$_2$ anti-mouse IgG and IgM conjugated to peroxidase (Tago, Burlingame, Calif.). Sixty μl of chromogen substrate (equal volumes of 2,2'anzino-di-(3-ethylbenzthiazoline sulfonate) and hydrogen peroxide; Kirkegaard and Perry) was added to each well. The plates were checked spectrophotometrically at 414 nm until the optical density reading of the 1:160 dilution of the positive control on the fusion protein-containing wells minus the background on the carrier protein-containing wells was equal to 0.5. The plates were then read immediately. A serum dilution was considered positive if the net absorbance (fusion protein well minus carrier protein well) was three standard deviations or more above the mean absorbance of the negative serum wells.

Monoclonal antibody to p23.

Monoclonal antibody (MAb) was produced by fusion of splenic cells from an immunized female Balb/c mouse 4–8 weeks old to NSO/1. The mouse was initially immunized with 200 μg of the fusion protein in DPBS emulsified in an equal volume of complete Freund's adjuvant (Difco Laboratories, Detroit, Mich.) supplemented with 5 mg/ml of desiccated *Mycobacterium tuberculosis* (Difco). The mouse received 5 booster injections every 2 weeks of 100 μg fusion protein in DPBS intraperitonally. Three days after the final injection, the spleen was harvested and a single-cell suspension of splenocytes were obtained over a fine-mesh stainless steel screen. Hybridomas were obtained essentially as previously described by St. Groth and Scheldegger, 1980. The fusion was performed with 50% (w/v) polyethylene glycol 1500 (Boehringer Mannheim, Indianapolis, Ind.) in 75 mM Hepes pH 8.01 at a spleen:myeloma cell ratio of 5:1. The cells were initially plated out at $5 \times 10^4$ myeloma cells per well of a 96-well flat bottom cluster tray (Costar, Cambridge, Mass.). Hybridomas were selected by growth for 14 days in medium containing complete medium (Dulbecco's modified eagle medium with 4500 mg/L D-glucose (Gibco), 2 mM L-glutamine, 100 U/ml penicillin G, 100 μg/ml streptomycin, 10% NCTC 109, $5 \times 10^{-5}$M 2-mercaptoethanol, and 10 mM Hepes supplemented with 20% of fetal calf serum (FCS) (Gibco) and $1 \times 10^{-4}$M hypoxanthine, $4 \times 10^{-7}$M aminopterin, $1.6 \times 10^{-7}$M thymidine (HAT) (Sigma). Subsequently, the cells were grown in complete medium with 20% FCS and HT (HAT medium without aminopterin) (Sigma) for 7 days followed by complete medium with 20% FCS. Supernatants from wells containing growing hybridomas were screened for selective reactivity with the fusion protein and not with the carrier protein in an ELISA. Hybridomas from antibody-positive wells were cloned twice by limiting dilution in 96-well trays using Balb/c thymus (one thymus per 60 wells) as a feeder layer.

Immunoelectron microscopy.

Spirochetes were removed from BSK II media by centrifugation at 7,000×g and 20° C. for 20 minutes and washed 2 times by centrifugation at 7,000×g and 10° C. for 20 minutes in Hank's balanced salt solution (HBSS) (Bio-Whitaker, Walkersville, Md.). Following the second wash, spirochete pellets were fixed for 30 minutes in 4% formaldehyde (Electron Microscopy Sciences, Ft. Washington, Pa.) in 0.1M sodium cacodylate buffer pH 7.4, to stabilize their outer membranes. Fixed pellets were washed 4 times in $Ca^{++}/Mg^{++}$-free phosphate buffered saline (PBS) and sequentially incubated in 0.1M glycine (pH 7.4) and PBS containing 1% bovine serum albumin (PBS-BSA) for 30 minutes each. Spirochete pellets were incubated with supernatant containing monoclonal antibody 4D7F5, a control isotype-matched mouse monoclonal antibody, or PBS-BSA alone for 2 hours at 20° C. Following three 5 minutes washes with PBS, spirochete pellets were incubated with goat anti-mouse IgG-10 nm gold conjugate (Amersham Life Sciences) diluted 1:20 in PBS-BSA, for 60 minutes at 20° C. Pellets were washed 3 times for 5 minutes with PBS and post-fixed with 2.5% glutaraldehyde (Electron Microscopy Sciences) in 0.1M sodium cacodylate buffer (pH 7.4). Pellets were osmicated, stained enbloc with uranyl acetate, dehydrated, and embedded in Spurr's resin. Thin sections were cut, stained with uranyl acetate and lead citrate and viewed in a Philips CM 10 transmission electron microscope.

RESULTS

Immunoblot analysis was performed on randomly selected sera from 79 patients who tested positive by ELISA for IgM reactivity to *B. burgdorferi*. The Connecticut strain 2591 was used as the source of antigen for both the ELISA and immunoblot studies. The bands most commonly seen on IgM immunoblot corresponded to proteins with molecular weights of 23 kDa, 41 kDa, 60 kDa, 66 kDa, and 31 kDa. The 23 kDa band was present in 98.7% (78/79) of the immunoblots. In 15% (12/79) of the specimens, the 23 kDa band was found in conjunction with either the 60 kDa or 66 kDa bands. The 23 kDa and 41 kDa bands occurred simultaneously in 82% (65/79) of the sera. The 41 kDa band was never present without the 23 kDa band.

Analysis of the strain 2591 sonicate by SDS-PAGE stained with Coomassie Blue demonstrated the expression of an abundant protein (p23) with a mobility corresponding to a molecular weight of approximately 23 kDa. Examination of the protein pattern from *B. burgdorferi* strain B31 isolated in North America demonstrated the lack of a detectable protein of 23 kDa. Both strains had been grown under the exact same conditions. An immunoblot of these electrophoretic patterns with serum from a patient with early Lyme disease demonstrated strong IgM reactivity to the 41 kDa flagellar antigen and relatively weak reactivity to 37, 39 and 75 kDa antigens from both strains. However, only with the strain 2591 sonicate was there detectable IgM reactivity with the 23 kDa protein. No additional antigen reactivity was detected in the lane containing the sonicate of strain B31.

An initial attempt to obtain a partial amino acid sequence of p23 by microsequencing of the protein after transfer to a polyvinylidenedifluoride membrane (Matsudaira, 1987) revealed a blocked amino-terminus. Therefore, p23 was purified from a preparative SDS-PAGE by electroelution for cleavage to allow isolation of internal fragments of the protein for sequencing. An initial attempt at chemical fragmentation with cyanogen bromide did not indicate a significant change in p23 mobility on SDS-PAGE. Consequently, the protein was digested with trypsin, and 2 resultant peptide fragments were isolated by reverse-phase HPLC and sequenced (the sequences of the 2 peptide fragments p1 and p2 are shown in FIG. 1). Comparison of the sequences of the 2 peptide fragments with published sequences of *B. burgdorferi* genes revealed p23 was homologous to the pC protein isolated from the European *B. burgdorferi* strain PKo (Fuchs et al., 1992). This homology permitted the synthesis of a pair of degenerate oligonucleotides in the appropriate orientation for amplification by PCR of a 104 bp product from strain 2591 genomic DNA. This product was radiolabeled and used as a probe for cloning of a 3 kb PstI fragment. DNA sequence analysis of the 3 kb PstI fragment identified an open reading frame encoding a 212 amino acid protein with an estimated molecular weight of 22,250 kDa (FIG. 2). An identical match between the predicted amino acid sequence of this gene and the sequence of both peptides confirmed this sequence to be the gene coding for p23. Comparison of p23 from strain 2591 with pC from strain PKo revealed 83% identity by nucleotide sequence and 75% identity by amino acid sequence (FIG. 2). These results strongly suggested p23 is a homologous protein to pC first isolated in Europe, with the differences between the two proteins representing interstrain divergence.

An additional 185 bp upstream of the AUG translation start codon of the p23 open reading frame were also sequenced (FIG. 1). Analysis of this region revealed a putative promoter containing consensus -35 and -10 hexamer sequences from *E. coli* (McClure, 1985) separated by 17 bp, as well as a consensus ribosomal binding site sequence (Gold et al., 1981) 9 bp upstream of the start codon.

To confirm whether the identified putative promoter sequence was the active site for transcription of p23, primer extension analysis was performed to ascertain the transcriptional start site. A 17-mer primer and RNA from strain 2591 was used. The major p23 transcript start site 20 bp upstream of the AUG translation start codon and 7 bp downstream from the -10 hexamer was mapped (FIG. 1). Longer exposure of the autoradiogram did not identify the presence of any longer transcript suggesting there were no additional upstream promoters significantly contributing to the transcriptional activity of the p23 gene.

Based on the determination of the complete coding sequence of p23, oligonucleotide primers were synthesized to amplify p23 by PCR from strain 2591 genomic DNA for expression in recombinant form. To avoid potential difficulty during isolation of the expressed protein, primers were selected so that the 20 amino acid residues comprising the leader peptide were deleted from the final recombinant product (Bassford et al., 1979; Fuchs et al., 1992). The amplified p23-encoding product was inserted in frame with the carrier protein of the expression vector pGEX-2T. After induction with IPTG, an approximately 46 kDa fusion protein was obtained. The fusion protein was purified from the *E. coli* lysate by use of glutathione agarose beads which bind to the carrier protein. To confirm identity of immunologic reactivity between native p23 and recombinant p23, patient serum with strong IgM reactivity to p23 from sonicate on an immunoblot was adsorbed with the fusion protein attached to glutathione beads. For controls, the serum was also adsorbed with glutathione beads alone and beads with only the carrier protein attached. Only adsorption with beads attached to the fusion protein removed completely the serum's reactivity to p23 on immunoblot. Adsorption did not affect the serum's reactivity to the other proteins on the blot.

Splenocytes from a mouse immunized with the p23-containing fusion protein were used to obtain hybridomas producing MAb to p23. Hybridoma supernatants were screened by ELISA for selective reactivity to the fusion protein and lack of binding to the carrier protein. Antibody from several of the hybridoma clones demonstrated particularly strong binding to both the fusion protein and native p23 on immunoblot. To determine the localization of p23, supernatant from one of these clones, 4D7F5 was selected for use in immunoelectron microscopy of strain 2591. p23 was found to be expressed on the outer surface of the spirochete. A control isotype-matched antibody did not bind. In addition, MAb 4D7F5 did not label strain B31 confirming the lack of expression of p23 by this strain.

The molecular reason for the lack of expression of p23 in strain B31 was studied as a result of the observation that B31 sonicate and whole organism did not react to sera and MAbs. Northern blot analysis for p23 mRNA revealed the strong expression of an approximately 700 bp transcript from strain 2591 and a very weak signal of the same size from strain B31. Examination of the RNA stained with ethidium bromide had revealed that an equivalent amount of RNA from each strain was loaded in the gel and that there was no appreciable degradation of the RNA. In addition, primer extension analysis also suggested a significantly reduced level of p23 mRNA in strain B31. Also, the size of the p23 primer extension termination product from strain B31 was found to be one base longer than the transcript from strain 2591. To gain a better understanding of the reason for the relative lack of p23 expression by strain B31, p23 gene was cloned and sequenced from strain B31 in the same fashion previously done for strain 2591. Comparison of the deduced amino acid sequences of p23 from strains 2591 and B31 as well as pC from PKo is shown in FIG. 2. p23 from strain B31 was found to contain 210 amino acids, 2 less than the other two homologs, and shares 80% amino acid sequence identity and 85% nucleotide sequence identity with p23 from strain 2591. Comparison of the proteins from the 3 strains showed conservation of sequence at the 5' (mostly leader peptide sequence) and 3' ends of the protein with increased variability in the central region.

Analysis of the B31 DNA sequence 5' to the coding region of p23 revealed a 54 bp deletion upstream to the consensus -10 and -35 promoter sequences found to be the active promoter region in strains 2591 and B31. The finding of this deletion in close proximity to the functional promoter region suggested the loss of an enhancing element which results in low transcriptional activity of p23 and lack of expression of the p23 protein in strain B31. The results suggest that nonexpressing strains of *B. burgdorferi*, such as B31, can be made to express the OspC protein by correcting the defect in the promoter region.

To confirm that the p23 gene from B31 could encode antigenic protein, the coding region of p23 was cloned into an expression vector and expressed in *E. coli* as a fusion protein. The recombinant p23 protein derived from strain B31 was as strongly reactive with sera and the MAbs as the native and recombinant forms of p23 from strain 2591.

Sera from fifteen patients with clinically suspected Lyme disease and positive IgM immunoblots with a minimum of 3 positive bands including reactivity to p23 were tested. All 15 of these sera were strongly positive by the recombinant p23 ELISA. Sera from 5 patients with syphilis, 10 patients with high titered rheumatoid factor, 5 patients with Epstein-Barr virus infection, and 10 patients with high titer antinuclear antibodies all tested negative with this assay. All of these sera also tested negative when examined by immunoblot with sonicate from strain 2591.

II. Clinical Study

Study groups.

Group I: sera from 74 individuals with EM from which *B. burgdorferi* had been cultured. This group included Group Ia: sera from 20 patients at the time of EM. These individuals could not give a reliable estimate of the duration of the rash but the rash was present when sera were obtained. Group Ib-d: sera from 54 individuals who were able to accurately state the number of days after onset of EM to the time sera was obtained. Group Ib: 19 sera at 1–7 days; Group Ic: 20 sera at 8–19 days; and Group Id: 15 sera at 20–90 days. All of the patients had received treatment with antibiotics upon presentation with EM.

Group II consisted of controls as follows: Group IIa: sera obtained from 20 normal individuals with no prior history of Lyme disease; Group IIb sera obtained from 50 normal volunteer donors living in a non-endemic area; and Group IIc sera from 6 patients with severe periodontitis. Patients with periodontitis have chronic exposure to high levels of oral spirochetes and usually develop antibodies which can cross-react with proteins from *B. burgdorferi* (Magnarelli et al., 1990). All sera were stored at −20° C. prior to analysis. Specimens were tested without knowledge of the status of the donor.

Whole Cell EIA.

The EIA for IgM and IgG anti-*B. burgdorferi* antibodies was performed as previously described with minor modifications (Magnarelli et al., 1984; Magnarelli et al., 1988). Briefly, *B. burgdorferi* strain 2591 spirochetes were collected from growth medium by centrifugation at 35,000×g for 35 minutes, washed 3 times, and resuspended in Dulbecco's phosphate buffered saline (DPBS; Sigma, St. Louis, Mo.) at a concentration of $10^6$ spirochetes/ml. Fifty μl of the spirochete solution was added to alternate wells of a 96-well, flat-bottom microdilution plate (Nunc-Immunoplate, Marsh Biomedical Products, Rochester, N.Y.). Fifty µl of DPBS was added to the remaining wells as a control for nonspecific binding. The plates were dried overnight at 37° C. prior to performing the assay. Patient sera were tested at dilutions of 1:160 and 1:320 in DPBS-0.05% Tween-20 (DPBS-T). Positive and negative control sera were also included on each plate. Goat anti-human IgG or IgM conjugated to horseradish peroxidase (Kirkegaard and Perry Laboratories, Gaithersburg, Md.) was used as secondary antibody. Plates were read when the net absorbance value (the difference in optical density between the antigen coated well and the DPBS-containing well) of the 1:160 dilution of the positive control serum was 0.5 for IgM and 1.0 for IgG. A test serum dilution was considered positive if the net absorbance value was 23 standard deviations above the mean net absorbance of the negative sera controls. Sera containing a positive dilution of ≧1:160 for IgM or ≧1:320 for IgG were reported as positive. Positive IgG-containing sera were further titered to endpoint by serial twofold dilutions to 1:5120. Further titration of positive IgM-containing sera was not performed.

Recombinant OspC ELISA.

ELISA to detect IgM antibodies to recombinant OspC (rOspC) was performed essentially as described above. Preliminary checkerboard titration studies with sera containing IgM antibodies to native OspC by immunoblot determined the optimal concentration of the recombinant OspC fusion protein to be 300 ng/well.

Immunoblot Assay.

The IgM and IgG immunoblot assay using a sonicate of *B. burgdorferi* strain 2591 was performed as described above with minor modifications. In brief, 60 µg of spirochetal proteins were electrophoresed in a discontinuous 12% polyacrylamide-sodium dodecyl sulfate gel (1.5 mm gel thickness, 8×18 cm plates, 130 mm preparative comb) using a vertical slab electrophoresis unit (Model SE 640, Hoefer Scientific Instruments, San Francisco, Calif.) at 22° C. for 2.5 to 3 hours at 120 volts with buffers described by Laemmli, 1970. Patient sera diluted 1:100 in PBS-T with 2% powdered non-fat milk was added to the nitrocellulose strips. Goat antihuman IgG and IgM conjugated to horseradish peroxidase (Sigma) and 3,3'-Diaminobenzidine (DAB) solution (50 mg/100 ml PBS and 10 µl of 40% hydrogen peroxide; Sigma) were used for antibody detection. Three different criteria for positivity on the IgM immunoblot were used: 1) ≧3 bands; 2) >3 bands, one of which had to be the 23 kDa protein; and 3) the 23 kDa protein±any other bands. For the IgG blot, 4 or more bands were considered positive.

Statistical Analysis.

The association between the length of duration after onset of disease and the rate of positive serologic result was evaluated by the chi-square test. The results of these studies are reported below in Tables 1–6.

TABLE 1

IgM reactivity in Group Ia Sera Drawn During EM

| Patient # | ELISA | | Immunoblot | | | | | | | |
|---|---|---|---|---|---|---|---|---|---|---|
| | WC | rOspC | 21 | 23 | 34 | 39 | 41 | 60 | 66 | kDa |
| 1. | − | − | | | | + | + | + | | |
| 2. | + | + | | + | | + | + | + | | |
| 3. | − | + | | + | | + | | + | | |
| 4. | + | + | + | + | + | + | + | + | + | |
| 5. | + | + | | + | | | + | + | | |
| 6. | − | − | | + | | | + | + | | |
| 7. | + | + | | + | | + | + | + | | |

TABLE 1-continued

IgM reactivity in Group Ia Sera Drawn During EM

| Patient # | ELISA | | Immunoblot | | | | | | | |
|---|---|---|---|---|---|---|---|---|---|---|
| | WC | rOspC | 21 | 23 | 34 | 39 | 41 | 60 | 66 | kDa |
| 8. | + | + | | + | | | + | + | | |
| 9. | − | + | | + | | + | + | | | |
| 10. | + | − | | | | | + | + | | |
| 11. | − | − | | | | | | | | |
| 12. | − | − | | | | | | | | |
| 13. | − | − | | | | | | | | |
| 14. | − | − | | | | | | | | |
| 15. | − | − | | | | + | | | | |
| 16. | − | + | | + | | | | | | |
| 17. | − | − | | | | | + | | | |
| 18. | − | − | | | | | + | | | |
| 19. | − | − | | | | | + | | | |
| 20. | − | − | | | | | | | | |

Nine of 20 sera from Group Ia patients were positive using the IgM immunoblot when 3 or more bands were used as the positive criteria (Table 1). Eight of the 9 sera with positive IgM immunoblots demonstrated reactivity with the 23 kDa protein. One serum which did not meet criteria for positivity was reactive with a single band of 23 kDa (patient #16). Six of 20 Group I a sera were positive using the IgM ELISA with whole cells (WC) of *B. burgdorferi* strain 2591, whereas 8 of the 20 sera were found to be reactive with the rOspC by ELISA. In 8 of 9 sera which demonstrated reactivity with the 23 kDa antigen on immunoblot, reactivity with rOspC by ELISA was also found.

For the Group Ib sera, 11 of 19 were positive by IgM immunoblot (Table 2). All 11 positive sera showed reactivity to the 23 kDa protein. None of the 8 negative sera demonstrated reactivity to the 23 kDa protein. There were 9 of 19 positive sera by WC IgM ELISA compared with 12 of 19 positive sera by rOspC ELISA.

TABLE 2

IgM Reactivity in Group Ib Sera Drawn 1–7 Days After Onset of EM

| Pt. # | ELISA | | Immunoblot | | | | | | |
|---|---|---|---|---|---|---|---|---|---|
| | WC | rOspC | 23 | 39 | 41 | 45 | 60 | 66 | kDa |
| 21. | − | + | + | | | | + | + | |
| 22. | − | + | + | | + | | + | + | |
| 23. | + | + | + | | + | | + | + | |
| 24. | + | + | + | | + | | | + | |
| 25. | + | + | + | | + | | + | + | |
| 26. | + | + | + | | + | | + | + | |
| 27. | + | + | + | | + | | + | + | |
| 28. | + | + | + | | + | + | + | + | |
| 29. | + | + | + | | + | | + | + | |
| 30. | + | + | + | + | + | + | + | + | |
| 31. | + | − | + | | + | | + | + | |
| 32. | − | − | | | | | | | |
| 33. | − | − | | | + | | | | |
| 34. | − | − | | | + | | | | |
| 35. | − | − | | | | | | | |
| 36. | − | − | | | | | | | |
| 37. | + | + | | | + | | | + | |
| 38. | − | − | | | | | | | |
| 39. | − | − | | | | | + | + | |

Seventeen of 20 Group Ic sera were positive by immunoblot (Table 3). All 17 samples contained antibodies which bound both the 23 kDa and 41 kDa proteins. Testing with the WC ELISA yielded 16 of 20 positive sera, whereas 17 of 20 sera tested positive by the rOspC ELISA. There was a perfect correlation between reactivity with the rOspC ELISA and the 23 kDa protein on immunoblot within this group.

TABLE 3

IgM Reactivity in Group Ic Sera Drawn 8–19 Days After Onset of EM

| Pt. # | ELISA WC | ELISA rOspC | Immunoblot 23 | 31 | 39 | 41 | 45 | 60 | 66 | 88 | kDa |
|---|---|---|---|---|---|---|---|---|---|---|---|
| 40. | + | + | + | | | + | | + | + | | |
| 41. | + | + | + | | + | + | + | + | + | | |
| 42. | − | + | + | | | + | | + | | | |
| 43. | + | + | + | | | + | | + | + | | |
| 44. | + | + | + | | | + | | + | + | | |
| 45. | + | + | + | | | + | | + | + | | |
| 46. | + | + | + | | | + | | | + | | |
| 47. | + | + | + | | | + | | + | + | | |
| 48. | + | + | + | | | + | | + | + | | |
| 49. | + | + | + | | | + | | | + | | |
| 50. | + | + | + | | | + | | + | + | | |
| 51. | + | + | + | | | + | | + | + | | |
| 52. | + | + | + | | + | + | | | + | | |
| 53. | + | + | + | + | | + | | + | + | | |
| 54. | + | + | + | | + | + | | + | + | + | |
| 55. | + | + | + | | | + | | + | + | + | |
| 56. | + | + | + | | + | + | | + | + | | |
| 57. | − | − | | | | + | | | | | |
| 58. | − | − | | | | | | | | | |
| 59. | − | − | | | | | | | | | |

Thirteen of the 15 Group Id sera were positive by IgM immunoblot (Table 4). There were 12 of 15 sera positive by the IgM WC ELISA and 10/15 positive sera with the rOspC ELISA.

TABLE 4

IgM Reactivity in Group Id Sera Drawn 20–90 Days After Onset of EM

| Pt. # | ELISA (IgM) WC | ELISA (IgM) rOspC | Immunoblot (IgM) 23 | 39 | 41 | 45 | 60 | 66 | 88 | kDa |
|---|---|---|---|---|---|---|---|---|---|---|
| 60. | + | + | + | | + | | + | + | | |
| 61. | + | + | + | | + | | + | + | | |
| 62. | + | + | + | | + | | + | + | | |
| 63. | − | − | + | | | | + | + | | |
| 64. | + | − | + | + | + | | + | + | | |
| 65. | + | − | + | | + | + | + | | + | |
| 66. | + | − | | | + | | + | + | | |
| 67. | + | + | + | | | | + | + | | |
| 68. | + | + | + | | | | + | + | | |
| 69. | + | + | + | + | + | + | + | + | | |
| 70. | + | + | + | | + | | + | + | | |
| 71. | + | + | + | | + | | + | + | | |
| 72. | + | + | + | | + | | + | + | | |
| 73. | − | − | | | | | | | | |
| 74. | − | + | | | + | | | | | |

For all three methods of testing, there was a statistically significant association between a longer disease duration and a greater frequency of a positive test (Table 5).

TABLE 5

Relation of Duration of EM to IgM Serologic Testing

| Test Group | # Patients | IB[c] (%+)[a] | ELISA WC[d] (%+) | ELISA rOspC[e] (%+) |
|---|---|---|---|---|
| Group Ia | 20 | 45 | 30 | 40 |
| Group Ib | 19 | 58 | 47 | 63 |
| Group Ic | 20 | 85 | 80 | 85 |
| Group Id | 15 | 87 | 80 | 67 |
| Group II (a–c) | 76 | 3[b] | 0 | 0 |

[a] defined as ≥3 bands
[b] one patient from non-endemic area, one patient with out history of Lyme disease
[c] the association between a longer disease duration and a greater frequency of a positive test was statistically significant $X^2 = 10.730$, 3 degrees of freedom, P = 0.013.
[d] $X^2 = 14.282$, 3 degrees of freedom, P = 0.003.
[e] $X^2 = 8.821$, 3 degrees of freedom, P = 0.032.

Conceivably, in some of the patients with Lyme disease and negative IgM reactivity, class switching of the anti-*B. burgdorferi* antibodies may have occurred. Therefore the sera was tested using IgG immunoblots and WC IgG ELISAs. Within Group Ia, only 1 of the 20 sera was positive for IgG immunoblot, and it was also positive on IgM immunoblot (patient #4). In one of these 20 sera the IgG WC ELISA was positive and the IgM WC ELISA was negative (patient #3). In Group Ib, 1 serum was positive by both IgM and IgG immunoblots (patient #31). One of the 3 Group Ic sera which tested negative by IgM immunoblot was reactive with the 23 and 41 kDa proteins on IgG immunoblot (patient #58). The other 2 IgM immunoblot negative sera showed reactivity to only the 41 kDa blot on IgG immunoblot. Both of the Group Id sera which were negative by IgM immunoblot were also negative by IgG immunoblot. There were no Group II sera which were positive by IgG immunoblot or IgG WC ELISA including the 2 samples found to be positive by IgM immunoblots.

To examine the specificity of the serologic testing, 76 control sera (Group II) were studied. Nineteen of the 20 Group IIa sera were negative by IgM immunoblot using the positive criteria of ≥3 bands. One serum bound 4 bands including the 41 kDa protein and the 23 kDa antigen. Three of the negative sera bound the 23 kDa protein. Twelve of the 20 serum samples contained reactivity with the 41 kDa protein. The WC and rOspC IgM ELISA were negative for all 20 samples.

Although these sera were obtained from normal donors without a history of Lyme disease, there was concern as to whether some individuals within this group were asymptomatically affected and thus have developed antibodies to *B. burgdorferi*. Based on this, an additional 50 sera obtained from normal volunteers from Iceland, a non-endemic area for Lyme disease (Group IIb) were issued. Only 1 of the 50 sera met criteria for a positive IgM blot (41,60,66 kDa bands). Twenty of the 50 sera demonstrated reactivity with the 23 kDa antigen on IgM immunoblot. None of the 50 samples were positive by the whole cell and rOspC IgM ELISA.

As an additional control group, sera obtained from 6 patients with severe periodontitis (Group IIc) were also studied. None of these sera were positive by IgM immunoblot using the positive criteria of ≥3 bands. Five sera reacted with the 41 kDa flagellar protein, and 3 sera had reactivity with the 23 kDa antigen. The 6 sera were negative for IgM reactivity with the WC and rOspC ELISA.

In Table 6, predictive values of the different serologic tests using the results obtained with the 74 Lyme disease sera and the 76 negative sera controls are compared.

TABLE 6

Comparison of IgM tests for Lyme disease

| | IB[1] | | | ELISA | |
|---|---|---|---|---|---|
| | ≥3 bands | 23 kDa +≥2 bands (%) | 23 kDa | WC[2] (%) | rOspC (%) |
| sensitivity | 68 | 65 | 66 | 58 | 64 |
| specificity | 97 | 99 | 64 | 100 | 100 |
| +predictive value | 96 | 98 | 64 | 100 | 100 |
| −predictive value | 76 | 74 | 66 | 71 | 74 |

[1]*B. burcidorferi* strain 2591 containing OspC (23 kDa) was used as source of antigen. Most North American strains do not express OspC.
[2]WC - whole cells used as source of antigen.

The results of the immunoblot analysis are analyzed using 3 different criteria for a positive test are presented. There were only 2 Lyme disease sera which did not bind the 23 kDa antigen, but still fulfilled criteria for a positive blot by binding 3 or more bands. There was only 1 example among the Lyme disease positive culture sera of binding to the 23 kDa protein but not binding 3 or more bands. Because of these infrequent findings there was no essential difference in the sensitivities of the IgM blots using the 3 different criteria for a positive assay. There was however, a significant drop-off in specificity when binding of the 23 kDa protein was used as the sole criteria for a positive blot. This reflects the relatively frequent observation of binding to the 23 kDa antigen among the negative sera controls. In contrast, there were no false positive results seen with the WC and rOspC ELISAs. A positive result with either of these 2 methods which use OspC, therefore, was superior to a positive result with immunoblot using the positive criteria of binding to the 23 kDa protein, for accurately predicting the presence of disease. The predictive value of a negative result was essentially equivalent with the three methods.

REFERENCES

Baranton, G. et al., *Int. J. Syst. Bacteriol.* 42: 378–383 (1992).
Barbour, A. G, *J. Biol. Med.* 57: 521–525, 1984.
Barbour, A. G. et al., *Infect. Immun.* 52: 549–554 (1986).
Bassford, P. J., Jr. et al., *J.Bacteriol.* 139: 19–31 (1979).
Bradford, M. M., *Anal. Biochem.* 72: 248 (1976).
Burgdorfer, W., et al. *Science,* 216: 1317–1319 (1982).
Coleman, J. L. et al., *J.Infect. Dis.* 155: 756–765 (1987).
Craft, J. E. et al., *J.Clin. Invest.* 78: 934–939 (1986).
Dattwyler, R. J. et al., Lancet 336: 1404–1406 (1990).
Dressler, F. et al., *J.Infect. Dis.* 167: 392–400 (1993).
Fuchs, R. et al., *Mol. Microbiol.* 6: 503–509 ( 1992) .
Gold, L. D. et al., *Ann. Rev. Microbiol.* 35: 365–403 (1981).
Hansen, K. et al., *Infect. Immun.* 56: 2047–2053 ( 1988).
Jones, K. A. et al., *Cell* 42: 559–572 (1985).
Laemmli, U. K., *Nature* 227: 680–685 (1970).
Magnarelli, L. A. et al., *J. Infect. Dis.* 156: 183–188 (1987).
Magnarelli, L. A. et al., *J. Clin. Microbiol.* 28: 1276–1279 (1990).
Magnarelli, L. A. et al., *J. Clin. Microbiol.* 20: 181–184 (1984).
Magnarelli, L. A. et al., *Am. J. Epidemiol.* 127: 818–825 (1988).
Magnarelli, L. A. et al., *J. Clin. Microbiol.* 30: 3158–3162 (1992).
Marconi, R. T. et al., *J. Bacteriol.* 175: 926–932 (1993).
Matsudaira, P., *J.Biol. Chem.* 262: 10035–10038 (1987).
McClure, W. R., *Ann. Rev. Biochem.* 54: 171–204 (1985).
McKnight, S. L and R. Kingsbury, *Science* 217: 316–324 (1982) .
Ozols, J., *J. Biol. Chem.* 265: 10289–10299 (1990).
Ozols, J. et al., *Methods in peptide and protein sequence analysis,* Birr(eds) Elsevier/North Holland Biomedical Press, Amsterdam, p. 417–429 (1980).
Russell, H. et al.; *J. Infect. Dis.* 149: 465–470 (1984).
Sadzlene, A. et al., *Infect. Immun.* 61: 2192–2195 (1993).
St. Groth, S. F. de and D. Scheldegger, *J. Immunol. Methods* 35: 1–21 (1980).
Steere, A. C., *N. Engl. J. Med.* 321: 586–596 (1989).
Steere, A. C. et al., *Ann. Intern. Med.* 99: 22–26 (1983).
Summers, W. C., *Anal. Biochem.* 33: 459–463 (1970).
Towbin, H. et al., *Proc. Natl.Acad. Sci. USA* 76: 4350–4354 (1979).
Wilske, B. et al., *J. Clin. Microbiol.* 31: 340–350 (1993).
Wilske, B. et al., *Infect. Immun.* 61: 2182–2191 (1993).
Wilske, B. et al., *Zbl. Bakt. Hyg. A* 263: 92–102 (1986).
Wilske, B. et al., *Annals of the New York Academy of Sciences.* Benach and Bosler (Eds.) New York Academy of Sciences, New York, N.Y.

EQUIVALENTS

Those skilled in the art will recognize or be able to ascertain, using no more than routine experimentation, many equivalents to the specific embodiments of the invention described specifically herein. Such equivalents are intended to be encompassed in the scope of the following claims.

I claim:

1. A method for the detection of early stage of Lyme disease, comprising the steps:

a) contacting recombinant or substantially pure form of outer surface protein C (OspC) from *Borrelia burgdorferi* sensu stricto, wherein said recombinant form of OspC has been produced by host cells which express OspC encoded by heterologous DNA, to a biological sample from a mammal suspected of having Lyme disease, wherein said sample is taken from the mammal at the early stage of infection; and b) detecting the presence or absence ok a complex formed between OspC and IgM antibodies, wherein the presence of an OspC/IgM complex is indicative of exposure to and infection by *Borrelia burgdorferi*.

2. The method of claim 1 wherein the biological sample is selected from the group consisting of serum, urine, tissue, cerebrospinal fluid, blood, pericardial fluid and synovial fluid.

3. A kit comprising recombinant or substantially pure form of outer surface protein C (OspC) from *Borrelia burgdorferi* sensu stricto, wherein said recombinant form of OspC has been produced by host cells, which express OspC encoded by heterologous DNA, and anti-human IgM conjugated to a detectable label for use in detecting the presence of IgM antibodies to the protein in a biological sample.

4. The kit of claim 3 further comprising *Borrelia burgdorferi* outer surface protein A, *Borrelia burgdorferi* outer surface protein B, *Borrelia burgdorferi* p41 and combinations thereof.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 824 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGGGAATTTA  GCATATTTGG  CTTTGCTTAT  GTCGATTTTA  AAATCAAATT  AAGTCAATAT    60

TTTTCAAATT  CTTCAATATT  TATTCAATAT  ATTGAATAAA  TTGAAAAAAT  TATTTTTTCA   120

AATAAAAAAT  TGAAAACAA   AATTGTTGGA  CTAATAATTC  ATAAATAAAA  AGGAGGCACA   180

AATTAATGAA  AAAGAATACA  TTAAGTGCAA  TATTAATGAC  TTTATTTTA   TTTATATCTT   240

GTAATAATTC  AGGGAAAGAT  GGGAATACAT  CTGCAAATTC  TGCTGATGAG  TCTGTTAAAG   300

GGCCTAATCT  TACAGAAATA  AGTAAAAAAA  TTACAGAATC  TAACGCAGTT  GTTCTCGCCG   360

TGAAAGAAGT  TGAAACTCTG  CTTGCATCTA  TAGATGAAGT  TGCTAAGAAA  GCTATTGGGA   420

ATTTGATAGC  CCAAAATGGT  TTAAATGCCG  GTGCTAATCA  AACGGATCA   TTGTTAGCGG   480

GAGCCTACGT  AATATCAACC  CTAATAGCAG  AAAAATTAGA  TGGATTGAAA  AATTCAGAAG   540

AATTAAAGGA  AAAAATTGAA  GATGCTAAAA  AATGTAACAA  AGCATTTACT  GATAAACTAA   600

AAAGTAGTCA  TGCGGAACTC  GGTATAGCGA  ATGGAGCTGC  TAGTGATGCT  AATGCAAAAG   660

CGGCTATTTT  AAAAACAAAT  GGTACTAAAG  ATAAGGGTGC  TCAAGAGCTT  GAAAAGTTAT   720

TTGAATCAGT  AAAAAACTTG  TCAAAGCAG   CTCAAGAAAC  ACTAAATAAT  TCAGTTAAAG   780

AACTTACAAG  TCCTGTTGTG  GCAGAAAATC  CAAAAAAACC  TTAA                    824
```

( 2 ) INFORMATION FOR SEQ ID NO:2:

( i ) SEQUENCE CHARACTERISTICS:
( A ) LENGTH: 212 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

```
Met  Lys  Lys  Asn  Thr  Leu  Ser  Ala  Ile  Leu  Met  Thr  Leu  Phe  Leu  Phe
 1              5                        10                       15

Ile  Ser  Cys  Asn  Asn  Ser  Gly  Lys  Asp  Gly  Asn  Thr  Ser  Ala  Asn  Ser
              20                       25                       30

Ala  Asp  Glu  Ser  Val  Lys  Gly  Pro  Asn  Leu  Thr  Glu  Ile  Ser  Lys  Lys
         35                       40                       45

Ile  Thr  Glu  Ser  Asn  Ala  Val  Val  Leu  Ala  Val  Lys  Glu  Val  Glu  Thr
     50                       55                       60

Leu  Leu  Ala  Ser  Ile  Asp  Glu  Val  Ala  Lys  Lys  Ala  Ile  Gly  Asn  Leu
65                       70                       75                       80

Ile  Ala  Gln  Asn  Gly  Leu  Asn  Ala  Gly  Ala  Asn  Gln  Asn  Gly  Ser  Leu
                   85                       90                       95

Leu  Ala  Gly  Ala  Tyr  Val  Ile  Ser  Thr  Leu  Ile  Ala  Glu  Lys  Leu  Asp
              100                      105                      110

Gly  Leu  Lys  Asn  Ser  Glu  Glu  Leu  Lys  Glu  Lys  Ile  Glu  Asp  Ala  Lys
         115                      120                      125

Lys  Cys  Asn  Lys  Ala  Phe  Thr  Asp  Lys  Leu  Lys  Ser  Ser  His  Ala  Glu
     130                      135                      140

Leu  Gly  Ile  Ala  Asn  Gly  Ala  Ala  Thr  Asp  Ala  Asn  Ala  Lys  Ala  Ala
145                      150                      155                      160

Ile  Leu  Lys  Thr  Asn  Gly  Thr  Lys  Asp  Lys  Gly  Ala  Gln  Glu  Leu  Glu
                   165                      170                      175

Lys  Leu  Phe  Glu  Ser  Val  Lys  Asn  Leu  Ser  Lys  Ala  Ala  Gln  Glu  Thr
              180                      185                      190

Leu  Asn  Asn  Ser  Val  Lys  Glu  Leu  Thr  Ser  Pro  Val  Val  Ala  Glu  Asn
         195                      200                      205
```

Pro Lys Lys Pro
      210

( 2 ) INFORMATION FOR SEQ ID NO:3:

( i ) SEQUENCE CHARACTERISTICS:
        ( A ) LENGTH: 210 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190

Asn Ser Val Lys Glu Leu Thr Ser Pro Val Val Ala Glu Ser Pro Lys
        195                 200                 205

Lys Pro
    210
```

( 2 ) INFORMATION FOR SEQ ID NO:4:

( i ) SEQUENCE CHARACTERISTICS:
        ( A ) LENGTH: 212 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Lys Lys Asn Thr Leu Ser Ala Ile Leu Met Thr Leu Phe Leu Phe
1               5                   10                  15

Ile Ser Cys Asn Asn Ser Gly Lys Gly Gly Asp Ser Ala Ser Thr Asn
            20                  25                  30

Pro Ala Asp Glu Ser Ala Lys Gly Pro Asn Leu Thr Glu Ile Ser Lys
        35                  40                  45
```

```
    Lys  Ile  Thr  Asp  Ser  Asn  Ala  Phe  Val  Leu  Ala  Val  Lys  Glu  Val  Glu
         50                      55                      60

Thr  Leu  Val  Leu  Ser  Ile  Asp  Glu  Leu  Ala  Lys  Lys  Ala  Ile  Gly  Gln
    65                      70                      75                           80

Lys  Ile  Asp  Asn  Asn  Asn  Gly  Leu  Ala  Ala  Leu  Asn  Asn  Gln  Asn  Gly
                        85                           90                      95

Ser  Leu  Leu  Ala  Gly  Ala  Tyr  Ala  Ile  Ser  Thr  Leu  Ile  Thr  Glu  Lys
                   100                      105                     110

Leu  Ser  Lys  Leu  Lys  Asn  Leu  Glu  Glu  Leu  Lys  Thr  Glu  Ile  Ala  Lys
              115                      120                     125

Ala  Lys  Lys  Cys  Ser  Glu  Glu  Phe  Thr  Asn  Lys  Leu  Lys  Ser  Gly  His
         130                      135                     140

Ala  Asp  Leu  Gly  Lys  Gln  Asp  Ala  Thr  Asp  Asp  His  Ala  Lys  Ala  Ala
    145                      150                     155                          160

Ile  Leu  Lys  Thr  His  Ala  Thr  Thr  Asp  Lys  Gly  Ala  Lys  Glu  Phe  Lys
                        165                     170                     175

Asp  Leu  Phe  Glu  Ser  Val  Glu  Gly  Leu  Leu  Lys  Ala  Ala  Gln  Val  Ala
                   180                      185                     190

Leu  Thr  Asn  Ser  Val  Lys  Glu  Leu  Thr  Ser  Pro  Val  Val  Ala  Glu  Ser
              195                      200                     205

Pro  Lys  Lys  Pro
              210
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GTATAAGGAG GTATGAAGAC     20

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CCGTTTCTGA GTTGATCGCG ATCCC     25

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTTTCCCTGA ATTATTA     17